United States Patent
Sripathirathan et al.

(10) Patent No.: US 10,945,995 B2
(45) Date of Patent: Mar. 16, 2021

(54) COMPOSITIONS AND METHODS FOR CHANNELOPATHY DISORDERS-TARGETING FLUID MOVEMENT ACROSS MEMBRANES

(71) Applicant: DEHA, LLC, Oklahoma City, OK (US)

(72) Inventors: Kumar Sripathirathan, Edmond, OK (US); Adhya Kumar, Edmond, OK (US)

(73) Assignee: DEHA, LLC, Oklahoma City, OK (US)

( * ) Notice: Subject to any disclaimer, the term of this patent is extended or adjusted under 35 U.S.C. 154(b) by 0 days.

(21) Appl. No.: 16/650,711

(22) PCT Filed: Sep. 25, 2018

(86) PCT No.: PCT/US2018/052689
§ 371 (c)(1),
(2) Date: Mar. 25, 2020

(87) PCT Pub. No.: WO2019/067458
PCT Pub. Date: Apr. 4, 2019

(65) Prior Publication Data
US 2020/0281898 A1 Sep. 10, 2020

Related U.S. Application Data

(60) Provisional application No. 62/563,434, filed on Sep. 26, 2017.

(51) Int. Cl.
| | |
|---|---|
| *A61K 31/4184* | (2006.01) |
| *A61K 31/343* | (2006.01) |
| *A61K 31/4196* | (2006.01) |
| *A61K 31/438* | (2006.01) |
| *A61K 31/4535* | (2006.01) |
| *A61K 31/506* | (2006.01) |
| *A61K 31/55* | (2006.01) |

(52) U.S. Cl.
CPC ........ *A61K 31/4184* (2013.01); *A61K 31/343* (2013.01); *A61K 31/4196* (2013.01); *A61K 31/438* (2013.01); *A61K 31/4535* (2013.01); *A61K 31/506* (2013.01); *A61K 31/55* (2013.01)

(58) Field of Classification Search
CPC .................................................. A61K 31/4184
USPC .................................................. 514/217.09
See application file for complete search history.

(56) References Cited

U.S. PATENT DOCUMENTS

2015/0133405 A1* 5/2015 Pelletier ............ A61P 3/12
514/119

FOREIGN PATENT DOCUMENTS

WO 2008052190 A2 5/2008

OTHER PUBLICATIONS

Stokum, Acta Neuropathologica Communications (2015) 3:61.*
Schwab, S., et al., The value of intracranial pressure monitoring in acute hemispheric stroke. Neurology 47, Feb. 1996, pp. 393-398.
Siegel, J. et al. "Update on Neurocritical Care of Stroke," Current cardiology reports 19:67, Jun. 2017, 11 pp.
Stankowski, J. N., et al. "Therapeutic targets for neuroprotection in acute ischemic stroke: lost in translation?" Antioxidants & redox signaling vol. 14, No. 10, 2011, pp. 1841-1851.
Stokum, J. A., et al., "Mechanisms of astrocyte-mediated cerebral edema," Neurochemical research vol. 40(2), Feb. 2015, pp. 317-328.
Stokum, J. A et al., "Heterogeneity of aquaporin-4 localization and expression after focal cerebral ischemia underlies differences in white versus grey matter swelling," Acta neuropathologica communications vol. 3:61, ,2015, 16 pp.
Sturdivant, N. M., et al., "Acetazolamide Mitigates Astrocyte Cellular Edema Following Mild Traumatic Brain Injury," Scientific Reports, vol. 6, Sep. 14, 2016, pp. 1-11.
Uldall, M., et al., "Acetazolamide lowers intracranial pressure and modulates the cerebrospinal fluid secretion pathway in healthy rats," Neuroscience Letters 645, Feb. 20, 2017, pp. 33-39.
Vahedi, K. et al., "Early decompressive surgery in malignant infarction of the middle cerebral artery: a pooled analysis of three randomised controlled trials," The Lancet Neurology 2007, vol. 6, Feb. 9, 2007, pp. 215-222.
Vella, J., et al., "The central role of aquaporins in the pathophysiology of ischemic stroke," Frontiers in Cellular Neuroscience, Apr. 8, 2015, vol. 9, Article 108, pp. 1-19.
Verkman, A. S., et al., "Aquaporins: important but elusive drug targets," Nature reviews Drug discovery vol. 13(4), Apr. 2014, pp. 259-277.
Wang, Z. et al., "Potential contribution of hypoxia-inducible factor-1alpha, aquaporin-4, and matrix metalloproteinase-9 to blood-brain barrier disruption and brain edema after experimental subarachnoid hemorrhage," Journal of molecular neuroscience, vol. 48, Apr. 22, 2012, pp. 273-280.
White, B. C. et al., "Brain ischemia and reperfusion: molecular mechanisms of neuronal injury," Journal of the neurological sciences vol. 179, Jul. 12, 2000, pp. 1-33.

(Continued)

*Primary Examiner* — Nizal S Chandrakumar
(74) *Attorney, Agent, or Firm* — Edwin S. Flores; Chalker Flores, LLP

(57) ABSTRACT

The present invention includes composition and methods for treating stroke comprising: identifying a subject in need of treatment for a stroke; and providing the subject with a therapeutically effective amount of an Aquaporin-4 inhibitor that blocks a filter portion of an Aquaporin-4 channel region, and identifying modulators of the different aquaporin specific splice variants.

8 Claims, 9 Drawing Sheets

(56) References Cited

OTHER PUBLICATIONS

Wijdicks, E. F., "Management of massive hemispheric cerebral infarct: is there a ray of hope?" Mayo Clinic proceedings 2000, 75, 945-952 (2000).
Yang, C. et al., "Aquaporin-4 knockdown ameliorates hypoxic-ischemic cerebral edema in newborn piglets," IUBMB life 67, Apr. 8, 2015, pp. 182-190.
Yao, X., et al., "Reduced brain edema and infarct vol. In aquaporin-4 deficient mice after transient focal cerebral schemia," Neuroscience Letters 584, Jan. 1, 2015, pp. 368-372.
Yu, H. et al., "Aquaporin 4 inhibition decreased synthesis of cytokines by acetazolamide in the hippocampus of rats with pentrazol-induced chronic epilepsy," Genetics and molecular research : GMR 15, Sep. 23, 2016, 12 pp.
Yukutake, Y., et al., "Rapid and reversible inhibition of aquaporin-4 by zinc," Biochemistry vol. 48, Nov. 21, 2009, pp. 12059-12061.
Yukutake, Y. et al., "Regulation of water permeability through aquaporin-4," Neuroscience 168, 2010, pp. 885-891.
Akdemir, G., et al., "Neuroprotective eftecty of aquaporin-4 deficiency in a mouse model of severe global cerebral ischemia produced by transient 4-vessel occlusion," Neurosci Lett. 2014, Jun. 27, 2015, vol. 574, pp. 70-75.
Alberga, D. et al. "A new gating site in human aquaporin-4: Insights from molecular dynamics simulations," Biochim Biophys Acta 1838, 3052-3060, doi:10.1016/j.bbamem.2014.08.015 (2014).
Alvarez-Leefmans, F., et al., "Use of ion-selective microelectrodes and fluorescent probes to measure cell volume," Methods in Neurosciences 27, 361-391 (1995), Summary only.
Ames, A., et al., "II. The No-Reflow Phenomenon," Cerebral Ischemia, Feb. 1968, pp. 437-453.
Choi, D. W. et al., "The role of glutamate neurotoxicity in hypoxic-ischemic neuronal death," Annual Review of Neuroscience 13, 171-182, doi:10.1146/annurev.ne.13.030190.001131 (1990).
Dostovic, Z., et al., "Brain Edema After Ischaemic Strok,". Med Arch vol. 70 No. 5, Oct. 2016, pp. 339-341.
Frank, J. I., "Large hemispheric infarction, deterioration, and intracranial pressure," Neurology vol. 45, Jul. 1995, pp. 1286-1290.
Grupke, S., et al., "Understanding history, and not repeating it. Neuroprotection for acute ischemic stroke: From review to preview," Clinical Neurology and Neurosurgery vol. 129, Nov. 13, 2014, pp. 1-9 (2015).
Hacke, W. et al. "Malignant middle cerebral artery territory infarction: clinical course and prognostic signs," Archives of Neurology 53, Dec. 7, 1995, pp. 309-315.
Haj-Yasein, N. N. et al., "Glial-conditional deletion of aquaporin-4 (Aqp4) reduces blood-brain water uptake and confers barrier function on perivascular astrocyte endfeet," Proceedings of the National Academy of Sciences of the United States of America 108, Sep. 22, 2011, pp. 17815-17820, doi:10.1073/pnas.1110655108 (2011).
Halgren, T., "New method for fast and accurate binding-site identification and analysis," Chem Biol Drug Des vol. 69, pp. 146-148, Feb. 2007.
Halgren, T. A., "Identifying and characterizing binding sites and assessing druggability," J Chem Inf Model 49, Sep. 8, 2008, pp. 377-389.
Hirt, L. et al., "Improved long-term outcome after transient cerebral ischemia in aquaporin-4 knockout mice," Journal of Cerebral Blood Flow and Metabolism vol. 37(1), Oct. 2015, pp. 277-290, (2017).
Ho, J. D. et al. "Crystal structure of human aquaporin 4 at 1.8 A and its mechanism of conductance," Proceedings of the National Academy of Sciences of the United States of America 106, 7437-7442, doi:10.1073/pnas.0902725106 (2009).
Igarashi, H.,et al., "Pretreatment with a novel aquaporin 4 inhibitor, TGN-020, significantly reduces ischemic cerebral edema," Neurological sciences : official journal of the Italian Neurological Society and of the Italian Society of Clinical Neurophysiology 32, Oct. 6, 2010, pp. 113-116, doi:10.1007/s10072-010-0431-1 (2011).
International Search Report and Written Opinion for PCT/US18/052689 by the USPTO dated Dec. 11, 2018, 9 pp.

Ishibashi, K., et al., "Aquaporin water channels in mammals," Clin Exp Nephrol 13, Dec. 16, 2008, pp. 107-117, doi:10.1007/s10157-008-0118-6 (2009).
Jin, B. J., et al., "Aquaporin-4-dependent K(+) and water transport modeled in brain extracellular space following neuroexcitation," The Journal of general physiology vol. 141 No. 1, pp. 119-132, doi:10.1085/jgp.201210883 (2013).
Kamegawa, A., et al., "Two-dimensional crystal structure of aquaporin-4 bound to the inhibitor acetazolamide," Microscopy (Oxford, England) 65, Nov. 2015, pp. 177-184, doi:10.1093/jmicro/dfv368 (2016).
Kasner, S. E. et al., "Predictors of fatal brain edema in massive hemispheric ischemic stroke," Stroke vol. 32, Jun. 26, 2001, pp. 2117-2123.
Katada, R. et al. "Greatly improved survival and neuroprotection in aquaporin-4-knockout mice following global cerebral ischemia," FASEB Journal, vol. 28(2), Oct. 24, 2013, pp. 705-714, (2014).
Lai, T. et al., "Excitotoxicity and stroke: identifying novel targets for neuroprotection," Progress in Neurobiology 115, Dec. 2013, pp. 157-188 (2014).
Manno, E. M., et al., "The effects of mannitol on cerebral edema after large hemispheric cerebral infarct," Neurology vol. 52(3), Feb. 1999, pp. 583-587.
Mehta, S. L., et al., "Molecular targets in cerebral ischemia for developing novel therapeutics," Brain research reviews vol. 54, Jan. 12, 2007, pp. 34-66.
Mehta, R. I. et al. "Sur1-Trpm4 Cation Channel Expression in Human Cerebral Infarcts," J Neuropathol Exp Neurol vol. 74 No. 8, Aug. 2015, pp. 835-849.
Mozaffarian, D. et al. "Heart disease and stroke statistics-2015 update: a report from the american heart association," Circulation 131, e29-e322, Jan. 27, 2015, doi:10.1161/cir.0000000000000152.
Noel, G., et al., "A high throughput screen identifies chemical modulators of the laminin-induced clustering of dystroglycan and aquaporin-4 in primary astrocytes," PLoS One 6, vol. 6, Issue 3, Mar. 7, 2011, e17559, 13 pp.
Ovbiagele, B. et al. "Forecasting the future of stroke in the United States: a policy statement from the American Heart Association and American Stroke Association," Stroke 44, pp. 2361-2375, Aug. 2013, doi:10.1161/STR.0b013e31829734f2.
Papadopoulos, M. C. et al., "Aquaporin-4 and brain edema," Pediatr Nephrol vol. 22, Mar. 9, 2007, pp. 778-784.
Parry, T. J. et al., "Effects of neuregulin GGF2 (cimaglermin alfa) dose and treatment frequency on left ventricular function in rats following myocardial infarction," Eur J Pharmacol 796, pp. 76-89, Dec. 16, 2016.
Powers, W. J. et al., "2015 American Heart Association/American Stroke Association Focused Update of the 2013 Guidelines for the Early Management of Patients With Acute Ischemic Stroke Regarding Endovascular Treatment: A Guideline for Healthcare Professionals From the American Heart Association/American Stroke Association," Stroke 46, Oct. 2015, pp. 3020-3035.
Previch, L. E. et al., "Progress in AQP Research and New Developments in Therapeutic Approaches to Ischemic and Hemorrhagic Stroke," International journal of molecular sciences 17, Jul. 18, 2016, pp. 1-16.
Pubmed Compound Summary for CID 42440144, 'VOIVWRBPHXEBTL-UHFFAOYSA-N', U.S. National Library of Medicine, May 30, 2009, pp. 1-11.
Pubmed Compound Summary for CID 72841291, 'BFAJDSPKRLLGJK-UHFFFAOYSA-N', U.S. National Library of Medicine, Feb. 28, 2014, pp. 1-11.
Pubmed Compound Summary for CID 91778307, 'ONGMEYWLKULUSB-UHFFFAOYSA-N', U.S. National Library of Medicine, Jun. 3, 2015, pp. 1-10.
Pubmed Compound Summary for CID 70738925, 'VCVOAQZCJSJABN-UHFFFAOYSA-N', U.S. National Library of Medicine, Mar. 4, 2013, pp. 1-11.
Pubmed Compound Summary for CID 25384356, 'LNDGJOMBSPGGSF-UHFFFAOYSA-N', U.S. National Library of Medicine, May 27, 2009, pp. 1-11.
Pubmed Compound Summary for CID 91781513, 'NTAMCQIV-VTYOLKO-UHFFFAOYSA-N', U.S. National Library of Medicine, Jun. 5, 2015, pp. 1-10.

(56) References Cited

OTHER PUBLICATIONS

Pubmed Compound Summary for CID 26224848, 'BNXRNISNKULBHX-IBGZPJMESA-N', U.S. National Library of Medicine, May 28, 2009, pp. 1-11.

Pubmed Compound Summary for CID 42500881, 'SDBWANBGOQGWSDUHFFFAOYSA-N', U.S. National Library of Medicine, May 30, 2009, pp. 1-10.

Pubmed Compound Summary for CID 70733552, 'YKQWGBSVIXKJAK-UHFFFAOYSA-N', U.S. National Library of Medicine, Mar. 4, 2013, pp. 1-11.

Rao, K. V., et al., "Aquaporin-4 expression in cultured astrocytes after fluid percussion injury," J Neurotrauma vol. 28, Mar. 2011, pp. 371-381.

Rash, J. E., et al., "Direct immunogold labeling of aquaporin-4 in square arrays of astrocyte and ependymocyte plasma membranes in rat brain and spinal cord," Proceedings of the National Academy of Sciences of the United States of America 95, Sep. 1998, pp. 11981-11986.

Remedy Pharmaceuticals. White paper: a guide to understanding large hemispheric infarction. (2016).

Dirnagl, U., et al., "Pathobiology of ischaemic stroke: an integrated view," Trends in Neurosciences, vol. 22, No. 9, 391-397 (1999).

\* cited by examiner

DEHA 35

DHA-6

DHA-37

DHA-36

COMPOSITIONS AND METHODS FOR CHANNELOPATHY DISORDERS-TARGETING FLUID MOVEMENT ACROSS MEMBRANES

CROSS-REFERENCE TO RELATED APPLICATIONS

This application is a National Stage of International Application of PCT/US2018/52689, filed Sep. 25, 2018, which claims the benefit of U.S. Provisional Application No. 62/563,434, filed Sep. 26, 2017. The contents of each of which are incorporated by reference in their entirety.

TECHNICAL FIELD OF THE INVENTION

The present invention relates in general to the field of compositions and methods related to treatment of water ion channel disorders.

BACKGROUND OF THE INVENTION

Without limiting the scope of the invention, its background is described in connection with methods for generating compounds that serve as modulators of water ion channels.

Diseases caused by channel dysfunctions are referred as channelopathies. Membrane channel proteins are responsible for movement of fluid across cellular compartments. Water is a major component of cells and tissues and is essential for cellular functions. Water channels embedded in lipid bilayer is crucial for facilitating water flow across cell membranes. The collective groups of proteins responsible for water transport across cell membranes are known as "Aquaporins". Aquaporinopathy refers to disorders resultant of water channel dysfunction and impaired fluid movement. Several sub-types of Aquaporin function are defective or materially altered and organs impacted have outcome that directly result in several disorders. More than dozen different classes of Aquaporin fluid transporters have been characterized. While majority of the aquaporins function as water channels, the physiological roles of many aquaporins are not clear. The present invention relates to the use of selective compounds as modulators of water ion channel for the prophylaxis, treatment and control of aquaporin mediated ion channel imbalance including water imbalance resulting in edema. Edema as an outcome of water imbalance occurs in multiple instances in particular of the brain and spinal cord following trauma or ischemic stroke. AQP-4 expressed highly in the brain is involved in stroke and several other nervous system disorders. While AQP-2 is involved in kidney function, function of AQP-6 and AQP-11 are not clearly established. Edema and related fluid imbalance is associated with central nervous system disorders including glioma, meningitis, epilepsy, stroke, traumatic brain injury, chronic traumatic encephalopathy, infection, cancer, cardiac, hepatic, ocular, otologic and renal disorders, diabetes, space travel, radiation exposure and metabolic disorders.

Stroke kills 130,000 Americans each year and is associated with an economic burden of $33 billion.[1] In the case of large infarctions, prognosis is poor due with rapid deterioration. This high rate of deterioration is generally associated with edema in the infarcted tissue.[2,3] Edema causes increased cranial pressure that can lead to cerebral herniation, brain damage, and death.[3-5] Current treatment strategies for brain edema include mannitol (osmotic agent) and other drugs such as barbiturates, steroids and diuretics (ion channel inhibitors) which do not address the direct underlying mechanism leading to brain edema—swelling caused by accumulation of water.[3,6] In severe instances of brain edema, surgery is the only option to relieve the increased pressure which is associated with high risk and increased cost.[2]

Other approaches currently under development for combating brain edema include, e.g., a drug designated BIIB093 was acquired by Biogen from Remedy Pharmaceuticals. The product was granted Orphan Drug Designation and Fast-Track designation by the FDA, supporting the significance of the unmet need for therapeutics to address brain edema in stroke. BIIB 093 is an anti-hyperglycemic sulfonylurea compound, which inhibits Sur1-Trmp4 channels that have been shown to play a critical role in cytotoxic edema, accidental necrotic cell death, blood-brain barrier breakdown, and formation of vasogenic edema.[4,6] Due to the small number of products under development the significant medical impact of brain edema, there is a great need of for the development of therapeutic agents that can provide an effective treatment option.

Despite many different efforts to prevent or reduce the effect of strokes, a need remains for novel compositions and methods for preventing, reducing, or eliminating the effect of strokes.

SUMMARY OF THE INVENTION

In one embodiment, the present invention includes a method of treating stroke comprising: identifying a subject in need of treatment for a stroke; and providing the subject with a therapeutically effective amount of an Aquaporin-4 inhibitor that blocks a filter portion of an Aquaporin-4 channel region. In one aspect, the Aquaporin-4 inhibitor is selected from at least one of:

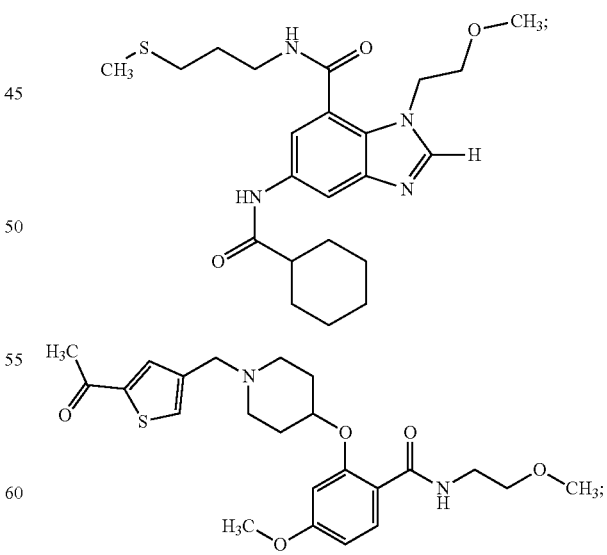

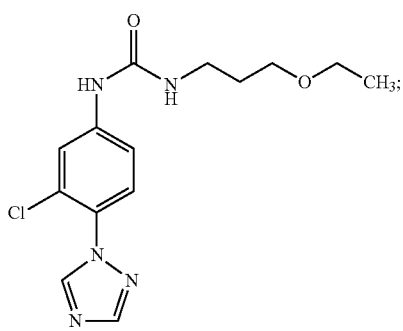

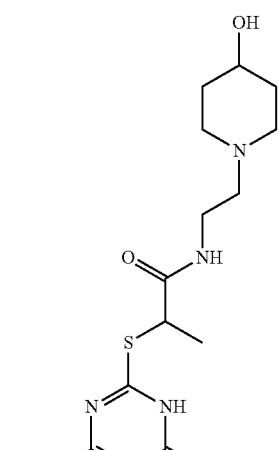

; or

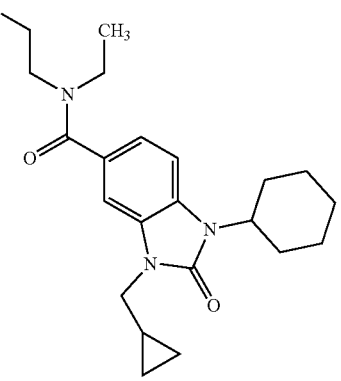

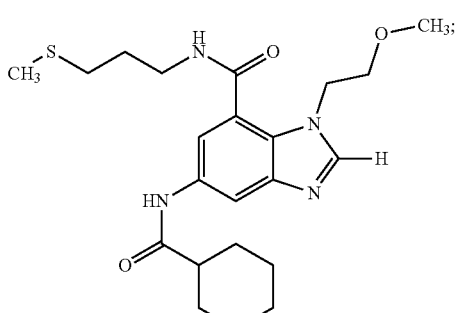

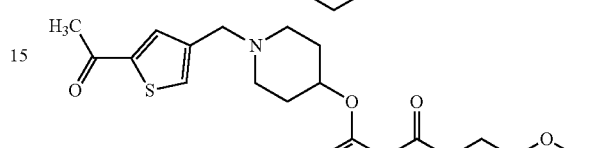

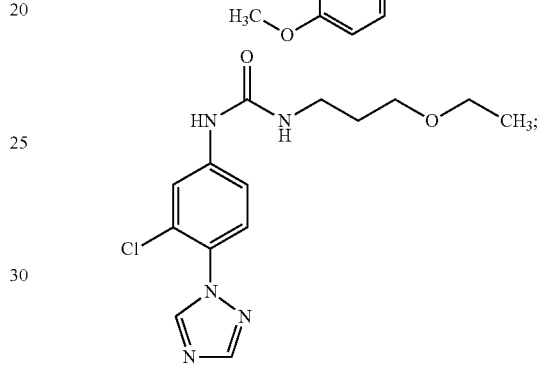

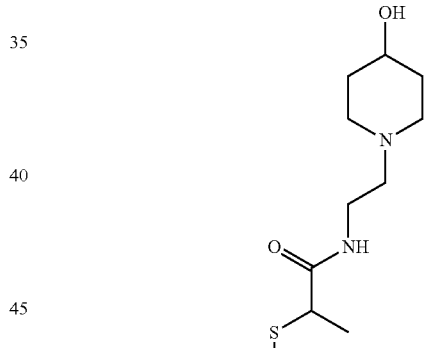

; or

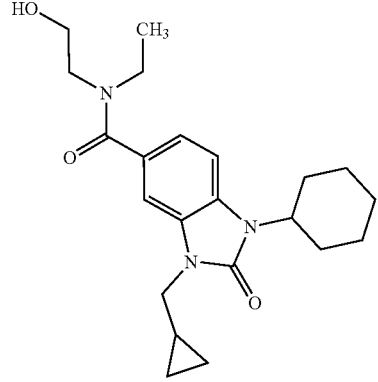

In another aspect, the Aquaporin-4 inhibitor is adapted for oral, enteral, parenteral, intravenous, subcutaneous, intramuscular, pulmonary, or rectal administration. In another aspect, the Aquaporin-4 inhibitor is provided in an amount of 1 microgram to 1 gram per dose. In another aspect, the patient has been treated previously with at least one of an osmotic agent, barbiturates, steroids, or diuretics and the subject has become refractory to that treatment. In another aspect, the Aquaporin-4 inhibitor has a potency in the range of 1-10 μM, 0.1-100 μM, or 5-9 μM. In another aspect, the Aquaporin-4 inhibitor inhibits perivascular astrocyte swelling. In another aspect, the Aquaporin-4 inhibitor reduces brain edema and infarct size after stroke.

In another embodiment, the present invention includes a composition for treating a stroke comprising: a pharmaceutically effective amount of an Aquaporin-4 inhibitor selected from at least one of:

In one aspect, the Aquaporin-4 inhibitor is adapted for oral, enteral, parenteral, intravenous, subcutaneous, intramuscular, pulmonary, or rectal administration. In another aspect, the Aquaporin-4 inhibitor is provided in an amount of 1 microgram to 1 gram per dose. In another aspect, the patient has been treated previously with at least one of an osmotic agent, barbiturates, steroids, or diuretics and the subject has become refractory to that treatment. In another aspect, the Aquaporin-4 inhibitor has a potency in the range of 1-10 µM, 0.1-100 µM, or 5-9 µM. In another aspect, the Aquaporin-4 inhibitor inhibits perivascular astrocyte swelling. In another aspect, the Aquaporin-4 inhibitor reduces brain edema and infarct size after stroke.

In another embodiment, the present invention includes a method of treating stroke comprising: identifying a subject in need of treatment for a stroke; and providing the subject with a therapeutically effective amount of an Aquaporin-4 inhibitor selected from at least one of:

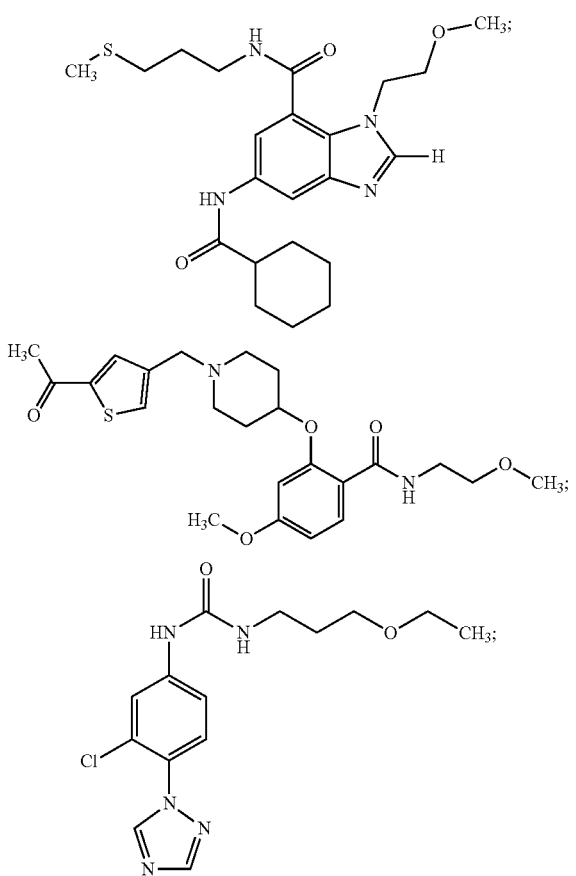

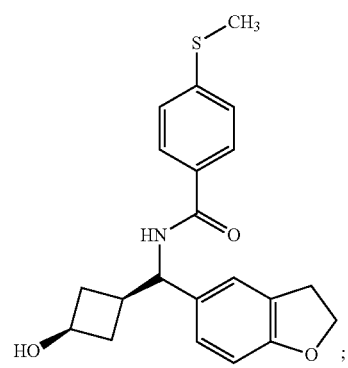

In one aspect, the Aquaporin-4 inhibitor is adapted for oral, enteral, parenteral, intravenous, subcutaneous, intramuscular, pulmonary, or rectal administration. In another aspect, the Aquaporin-4 inhibitor is provided in an amount of 1 microgram to 1 gram per dose. In another aspect, the patient has been treated previously with at least one of an osmotic agent, barbiturates, steroids, or diuretics and the subject has become refractory to that treatment. In another aspect, the Aquaporin-4 inhibitor has a potency in the range of 1-10 µM, 0.1-100 µM, or 5-9 µM. In another aspect, the Aquaporin-4 inhibitor inhibits perivascular astrocyte swelling. In another aspect, the Aquaporin-4 inhibitor reduces brain edema and infarct size after stroke.

In another embodiment, the present invention includes an Aquaporin modulator selected from at least one of:

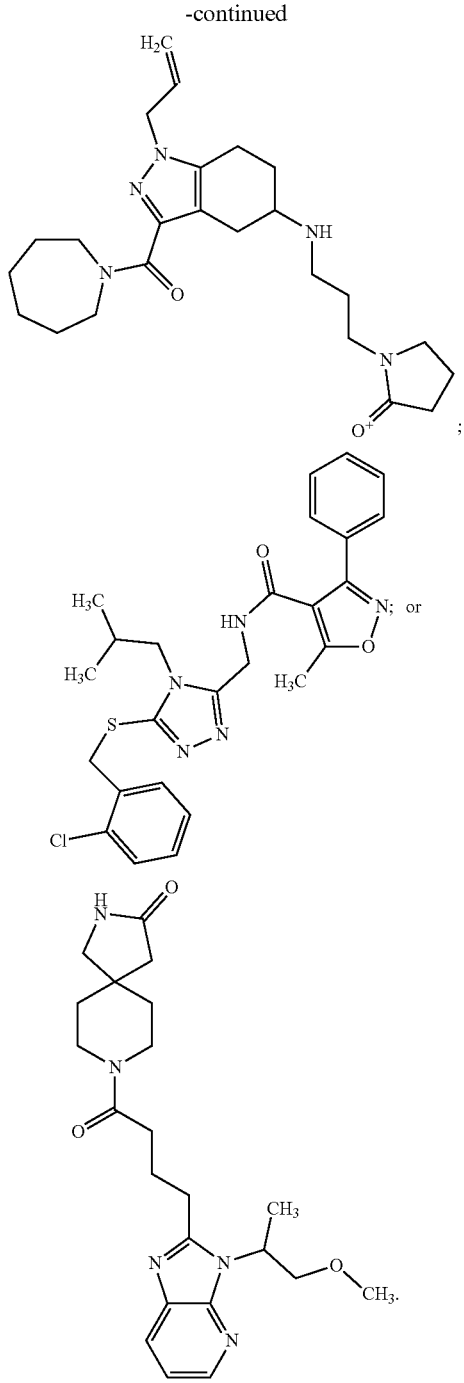

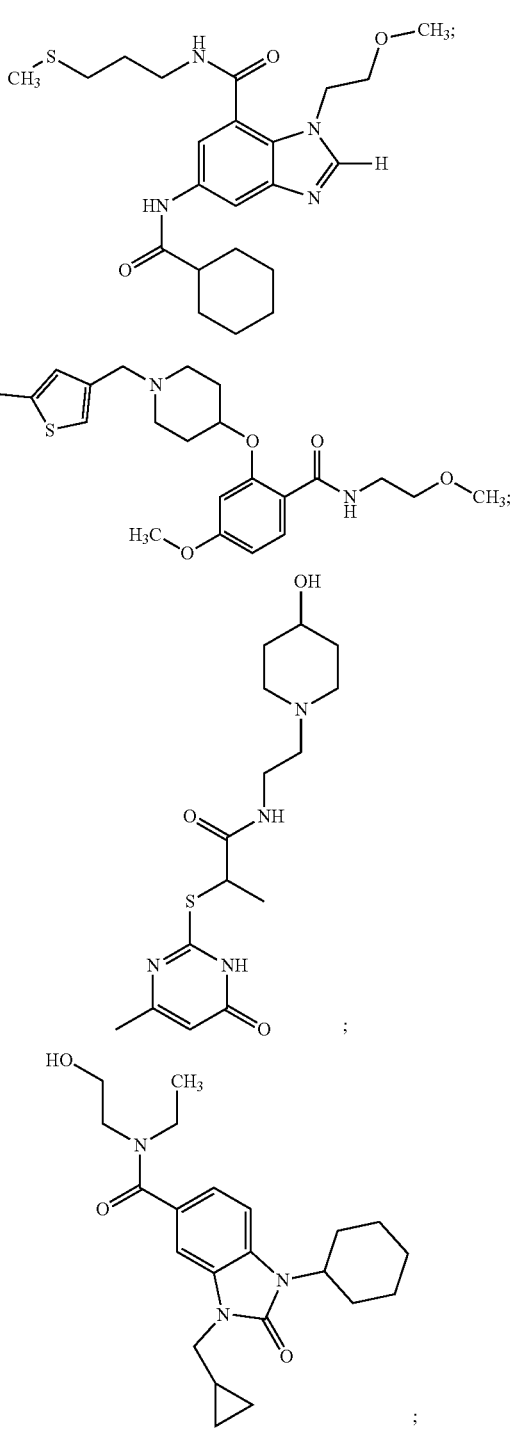

In one aspect, the Aquaporin is an Aquaporin-2, an Aquaporin-6, or an Aquaporin-11.

In another embodiment, the present invention includes a method of treating a subject in need of treatment for a disease or condition in which an Aquaporin-2, an Aquaporin-6, or an Aquaporin-11 is in need of modulation comprising: identifying a subject in need of treatment for the disease or condition in need of modulation of an aquaporin; and providing the subject with a therapeutically effective amount of an Aquaporin-2, an Aquaporin-4, an Aquaporin-6, or an Aquaporin-11, inhibitor or modulator selected from at least one of:

-continued

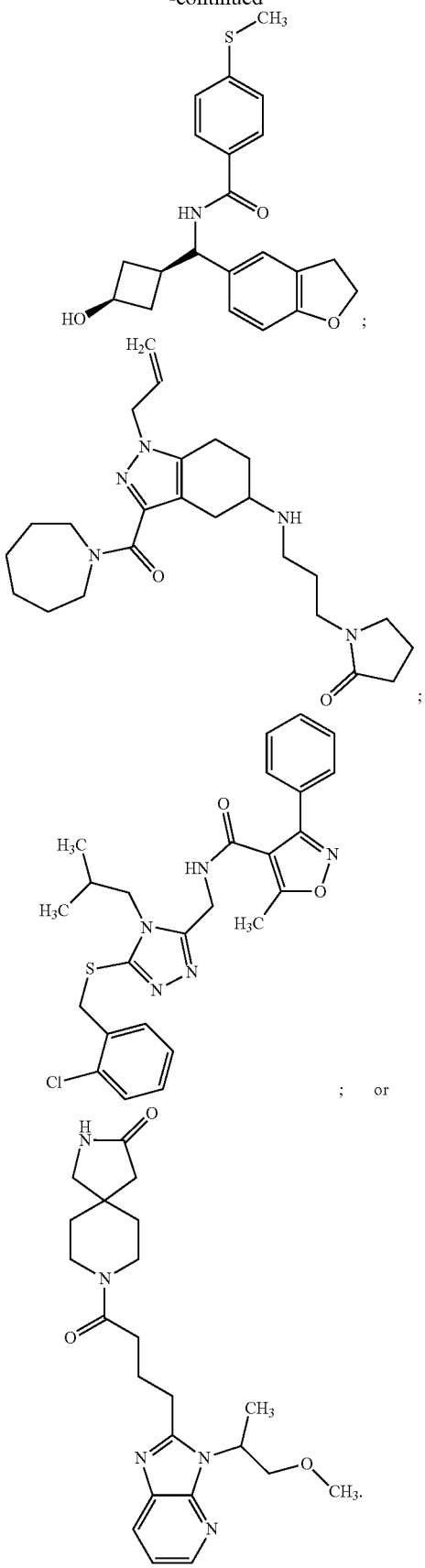

; or

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figures 1A, 1B:
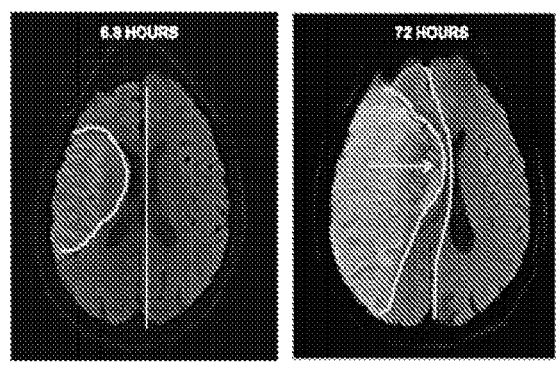
FIGS. 1A and 1B are images of a patient who developed edema that was severe enough to push the brain midline over more than 1.5 cm. The patient subsequently died.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present inventors recognized that brain edema is the result of increased permeability of the water channel protein, Aquaporin-4 (AQP-4). AQP-4 is the most abundant brain aquaporin and is expressed highly in the brain and upregulated in edema and related pathologies.[7] Studies investigating brain edema in AQP-4 null mice have shown that they fare better after ischemic insult than do wild type mice.[8] Given these observations, the present inventors have identified and characterized novel inhibitors of AQP-4, that can be used in an ischemic insult to greatly reduce brain damage through the prevention of brain edema.[9,10] Only a few inhibitors have been identified that target the mouth of the AQP-4 pore, and there are currently no AQP-4 inhibitors in clinical development.[11]

The present inventors have developed a small molecule therapeutic approach for treating cytotoxic edema by inhibiting a specific, targeted portion of AQP-4. Structure-based computational screens of compound libraries was conducted, followed by experimental validation using an in vitro cell swelling assay have successfully identified hits with diverse structural scaffolds. The potency of the compounds range 5-9 µM. These compounds are the scaffolds from which the potency and pharmaceutical properties can be improved. Thus, the present invention includes at least 5 new classes of molecular scaffolds that lead to AQP-4 inhibitors for controlling cellular swelling. These scaffolds can be further optimized for potency and pharmaceutical properties.

The present inventors used in silico high throughput docking (HTD)-based virtual screening combined with solvation model-based binding energy (MM-GBSA) calculations to assess target binding of derivatives with the core scaffolds identified in preliminary studies. Through this in silico process, compounds were ranked according to predicted binding strength and approximately 50 derivatives were synthesized based on these chemical scaffolds. Derivatives then undergo in vitro assessment and pharmacokinetic evaluation of leads. First, 50 candidate AQP-4 inhibitors were evaluated for effects on cell swelling.

Figure 2:
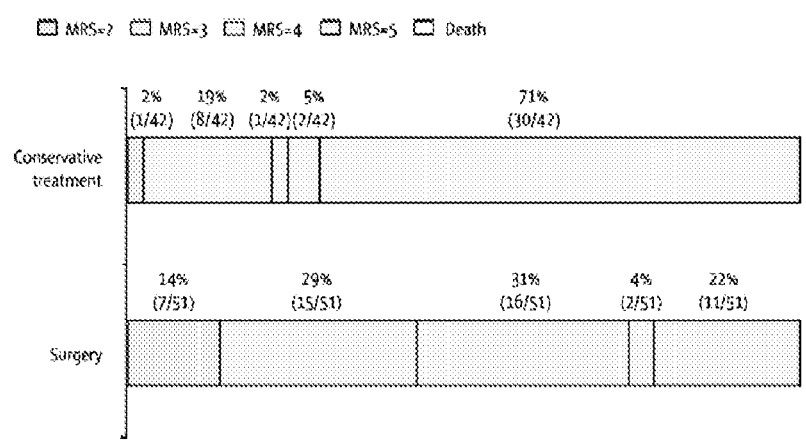
FIG. 2 shows a distribution of neurological disability scores using modified Rankin scale (MRS) after 12 months for patients treated with or without decompressive surgery.

Role of cerebral edema in stroke. Large hemispheric infarctions affecting the total or sub-total territory of the middle cerebral artery represent a minority of strokes (14%), yet they are responsible for the disproportionately large share of stroke-related morbidity and mortality. While the overall mortality rate for stroke is 8%-10%, the mortality rate for large hemispheric infarctions ranges from 40% to 80%.[2,21] Early deterioration and death in these large-territory strokes occurs due to brain edema within the rigid skull (FIGS. 1A and 1B). Edema causes mass-effect with distortion, tissue shift, and increased intracranial pressure, leading to cerebral herniation, further brain damage and death.[4,5] Existing treatments are limited to elevating the patient's head and administering mannitol, hypertonic saline, or glycerol.[6,22] All three agents act by increasing serum osmotic gradient to pull cerebral water into the bloodstream. Decompressive hemicraniectomy is a highly invasive surgical alternative that has been shown to improve survival; however, the method is associated with a high risk of severe neurological disability (FIG. 2).[20] Given the moderate effectiveness of current therapeutic options for brain edema and their associated risks, there is a significant unmet need for effective pharmacotherapies targeting brain edema.

Role of aquaporins in stroke. The complex pathophysiology of stroke and its molecular mechanisms have been extensively researched.[23-25] Cerebral edema formation in the acute phase has been linked to the water channel proteins aquaporins, and specifically to aquaporin-4 (AQP-4).[7,26,27] AQP-4 is a passive, bidirectional water-specific channel expressed throughout the brain and the spinal cord, and is the predominant aquaporin in astrocyte end-feet which tightly wrap around capillaries.[28] AQP-4 is principally responsible for the osmotic water influx in cytotoxic edema, which results from disrupted ionic gradients caused by ischemic energy depletion.[7] Astrocytes likely become overloaded with glutamate and potassium, triggering water influx and subsequent swelling. This in turn can initiate secondary effects which further exacerbate brain damage. Swelling perivascular astrocytes may compress blood vessels thus limiting vascular circulation (i.e. "no-reflow" phenomenon[29]), and release glutamate through volume-regulated ion channels. The reduction in extracellular space can additionally raise excitotoxic glutamate concentrations.[30] These findings are supported by studies in animal stroke model; AQP-4 deletion in mice reduces brain edema and infarct size after stroke, greatly improving survival and functional outcomes.[31-36] Similar effects on edema were observed with AQP-4 antibody blockade in a rat subarachnoid hemorrhage model[37], and using siRNA AQP-4 knockdown in a piglet hypoxia-ischemia model.[38] A study of postmortem human tissues showed that following ischemia, AQP-4 abundance in subcortical white matter increased by 2.2- to 6.2-fold. Concurrently, white matter was swollen by 42.5±8.84%, in contrast to cortical grey matter which was swollen by 8.95%±2.64%, in agreement with prior studies demonstrating the susceptibility of white matter to swelling after acute injury.[39]

Targeting AQP-4 in brain edema. Aquaporins have proven themselves to be challenging drug targets. As passive channels, they lack gating and transport mechanisms that could be exploited (although AQP-4 is pH-sensitive), and because they transport small neutral molecules, electrostatic interactions are limited, and the pore channel is small.[10] Furthermore, the widely used water permeation assays utilizing Xenopus oocytes are prone to artifacts and yielded false-positive results when used in screening putative AQP-4 inhibitors drug candidates (aryl sulphonamides, anti-epileptics, auto-antibodies).[10] Clinically useful AQP-4 inhibitors have been not yet been identified; however, TGN-020 (2-(nicotinamide)-1,3,4-thiadiazole) pre-treatment was reported to reduce edema and infarct size in a mouse model of stroke by reducing AQP-4 permeability.[40] Several AQP-4 inhibitors have shown positive results in animal models (e.g. edavarone, piroxicam); however, work by decreasing AQP-4 expression, rather than permeability.[27] Acetazolamide, initially identified as a AQP-1 inhibitor,[41] has been shown to inhibit AQP-4 in independent in vivo studies in a rat model of epilepsy[42] and reduce edema (and increase AQP4 expression) in a rat traumatic brain injury model.[43] A crystal structure of AQP-4 in complex with acetazolamide has been published;[44] however, acetazolamide may also lower intracranial pressure by inhibiting the Na/K ATPase to slow the CSF production[45], making its effects of acetazolamide on edema less clear.

As described above, the link between brain edema and AQP-4 is well-established. However, despite this strong scientific premise, inhibitors that specifically target AQP-4 are lacking due to inhibitors' having inherent non-aquaporin activities. The present invention addresses the profound unmet medical need in treating cerebral edema following stroke by building upon the strong scientific evidence of AQP-4's role in CNS edema pathology to identify small molecule inhibitors that specifically target AQP-4. The strategy used large structural biology data (X-ray crystallography, molecular dynamics) to leverage the mechanism of water transport through AQP-4 pore at the molecular level in identifying molecules that specifically target the AQP-4 channel.

Figure 3:
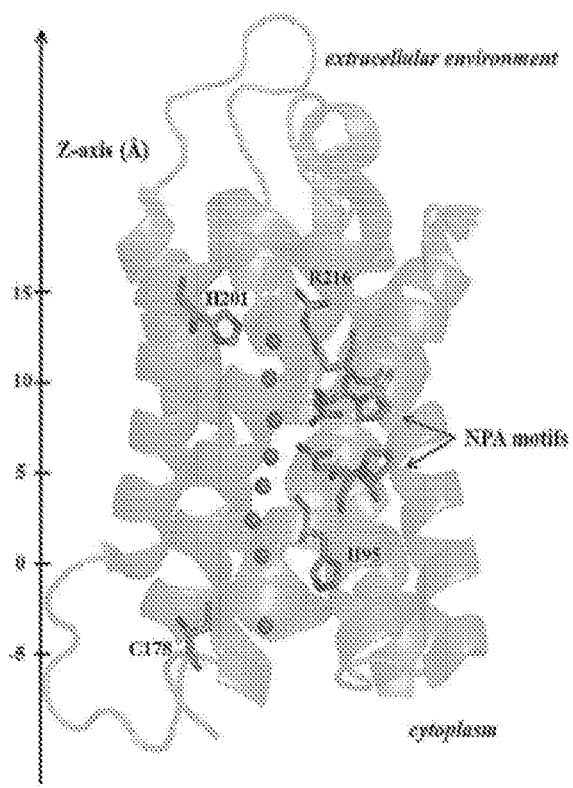
FIG. 3 is a structure for human AQP-4. Residues involved in water permeability are noted. Water molecules are depicted as red spheres.

Studies have shown that water permeability through AQP-4 is regulated by two NPA (asparagine, proline and alanine) motifs that comprise a filter region in the middle of the channel. These motifs, in addition to region known as the selectivity filter, are responsible for water selectivity through a spatial restriction mechanism. The control of water flux has been attributed to gating mechanisms. Using molecular dynamics simulations, Alberga et al. identified a gating mechanism located on the cytoplasmic side of the protein that is formed by two residues, C178 and H95 (FIG. 3)[40]. The H95 residue was shown to serve as a molecular switch through the reorientation of its imidazole ring allowing for a hydrogen bonding interaction with C178 creating a decrease in water flux rate.[47] The importance of the C178 residue in water permeability was supported by the inhibition of AQP-4 by divalent cations through interaction with C178.[48,49]

First, the present inventors in silico screened 500,000 small-molecules, and selected molecules that bind to a pocket near intracellular loops of the channel that will be AQP-4-selective and high-affinity binders. There are only two potential binding pockets on the AQP-4 protein (as identified by SiteMap, a binding pocket identification program), located on either side of water channel pore. The inventors initially targeted the intracellular-side pocket for its proximity to H95 gate-keeper residues, which is shown to control the diameter of water channel by hydrogen bonding with C178 residue, and decreases the water permeability[40].

However, reported AQP-4 inhibitors are either too small in size to block the AQP water channel effectively or they are not designed to be bind to AQP-4 selectively. Thus, the inventors novel molecular screening approach was designed to take advantage of molecular mechanism of water permeability and predicted to bind in T-shape form so that top line (horizontal line in T) binds to mouth of pocket ("lid"), while vertical line (that butts up against the T's top) interacts deep inside of pocket reaching out to H95 side chain (similar to a "cork" closing a bottle). Utilizing this approach the present inventors have identified molecules of structurally diverse scaffolds that exhibit drug-like properties. Using hits from this screen, the inventors can use medicinal chemistry approaches, guided by structure based design, to optimize hit molecules for target engagement and in vivo assessment. Unlike the antihyperglycemic compounds that have metabolic consequences, the compounds disclosed here are selective for AQP-4. By administering the drug IV route, brain edema is expected to be quickly resolved without consequences impacting the glymphatic circulation. The target product is expected to be present in patients for less than 10 days.

Successful development of an AQP-4 inhibitor by the present inventors will greatly enhance the clinical outcomes of patients that have suffered from a stroke and subsequent cerebral edema. While the development of an AQP-4 inhibitor would address an unmet need for these patients, it has a wider therapeutic impact in a host of central nervous system pathologies, traumatic brain injury, liver encephalopathy and other disorders causing brain edema.

Figure 4:
FIG. 4 is a structure that shows the binding of a representative scaffold compound of interest as viewed using Schrodinger software.

In silico screening of molecular libraries. To identify in silico hits for AQP-4 inhibition that bind tightly and block the AQP-4 water channel (FIG. 4), the inventors identified a binding pocket near intracellular loops of AQP-4 structure (PDB code: 3GD8),[50] using the SiteMap program from Schodinger.[51,52] A final subset of 50 compounds was purchased for experimental verification in a calcein-fluorescence cell swelling assay.

Figure 5:
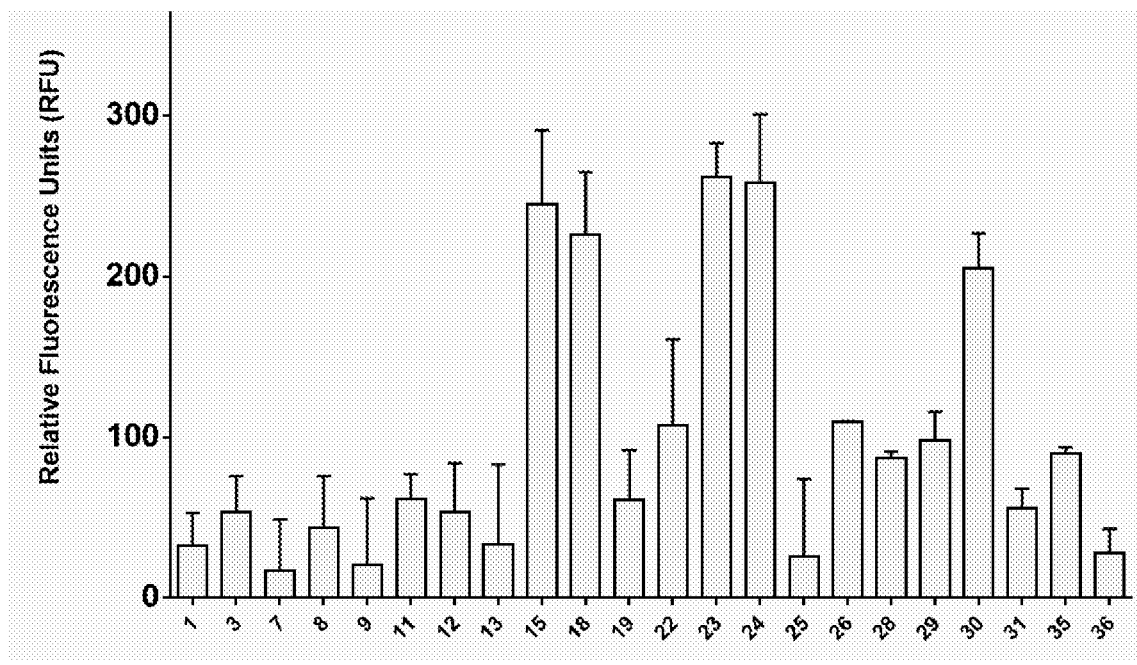
FIG. 5 is a graph that shows the relative fluorescence intensity of several compounds that were assessed in initial calcein-AM screening efforts.
Figure 6A:
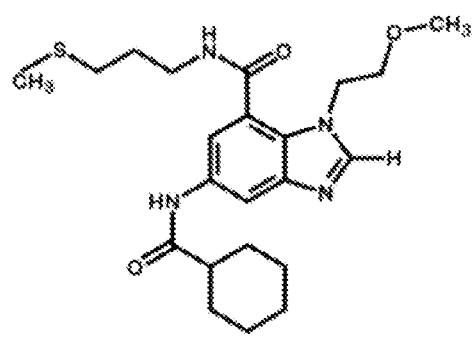
FIGS. 6A to 6E show the initiation scaffold compounds of the present invention.
Figure 6B:
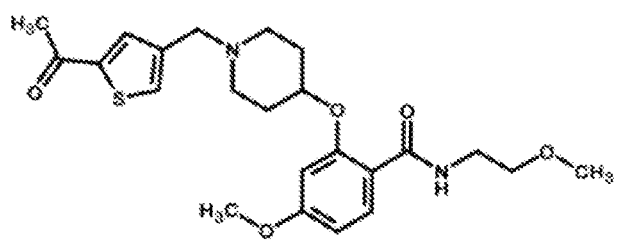
Figure 6C:
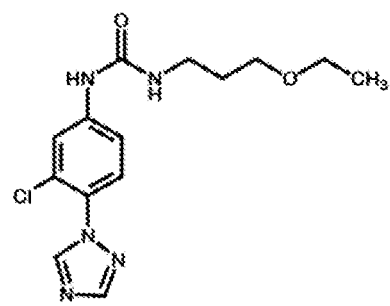
Figure 6D:
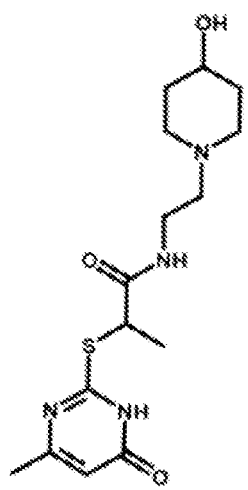
Figure 6E:
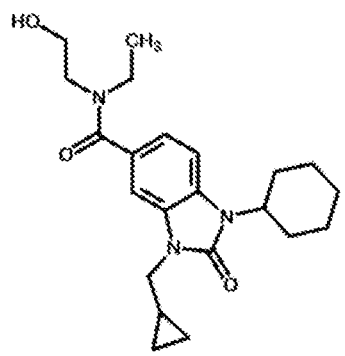

Effects of candidate AQP-4 inhibitors on cell swelling in vitro. Kinetic screening assay: In order to assess the effects of the resulting 50 compounds selected from in silico screening efforts on cell swelling, a calcein-fluorescence assay that measures plasma membrane water permeability was used. Alvarez-Leefmans et al. established a technique to estimate changes in cell volume as a function of changes in concentration using a calcein-AM, a non-fluorescent and membrane-permeant dye.[53] After entering the cell, calcein-AM is converted to calcein by removal of the acetoxymethyl group (AM) by intracellular esterases. Calcein is fluorescent and cell-impermeant, becoming trapped once inside the cell. When cells are exposed to hypotonic solution they swell, increase their volume, thus decreasing the concentration of calcein and, consequently, the intensity of its fluorescent signal in a manner directly proportional to the dye concentration. The opposite happens when they are exposed to a hypertonic solution. The fluorescence signal is calibrated by brief exposures of the calcein-loaded cells to, for example, 15% hypotonic and 15% hypertonic solutions and the average signal intensity from the cell is detected. To use this assay for identifying AQP-4 inhibitors, human colorectal cells (HCT-116) were loaded with calcein-AM for 30 min at 37° C. The test compounds were then added (4-9 µM) and the fluorescence was measured using a Biotek plate reader (excitation 490 nm and emission 515 nm). Relative fluorescence intensity (RfU) was calculated as the fluorescence intensity of each well divided by the mean fluorescence intensity of cells treated with DMSO (control). Compounds with RfU values >200 were deemed promising compounds of interest. From initial screening, several leads were identified that had an RfU of >200 (FIG. 5). FIGS. 6A to 6E show the structures of compounds of the present invention.

Figure 7A:
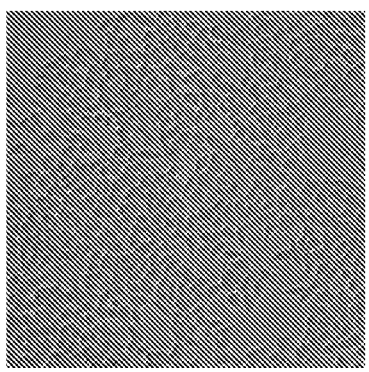
FIGS. 7A to 7C shows cells overexpressing hAQP-4 protein challenged with water (5 min) that show rapid swelling monitored over a 5 min time period.
Figure 7B:
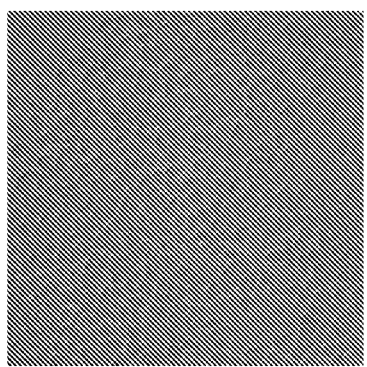
Figure 7C:
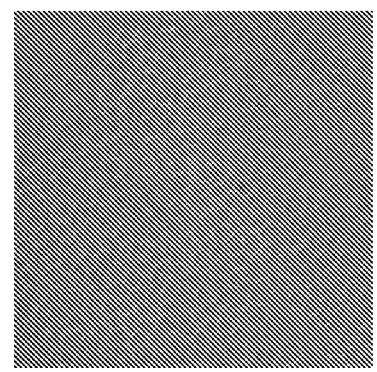
Figure 8:
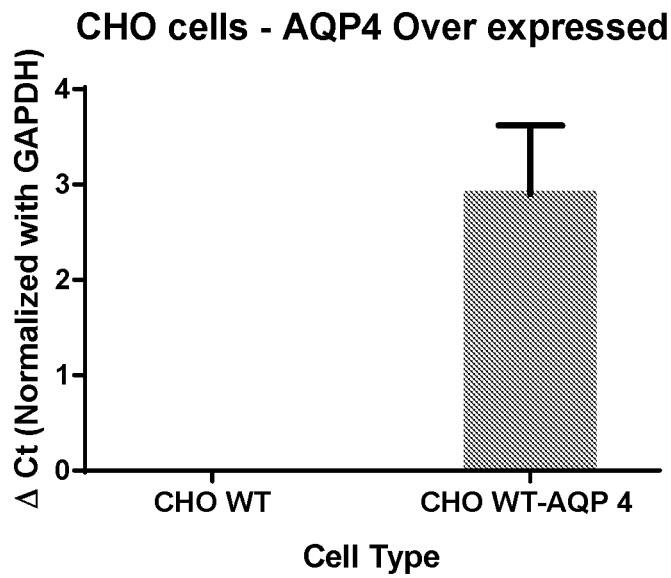
FIG. 8 shows confirmation by PCR of AQP-4 overexpression in CHO transfected cells compared to wild type cells.

Aquaporin specificity of the compound: High throughput end point assay—Engineering CHO cells to overexpress human AQP-4. CHO cells were transfected with hAQP-4. CHO-K1 cells were engineered to express AQP-4 using the method described by Yang et al., 2015 and selection of clones were made for cells overexpressing hAQP-4. Cell swelling was evaluated by identifying cell volume changes following hypotonic solution exposure. Cells expressing hAQP-4 swell more rapidly than control cells due to increased water flow. Cells challenged with water (5 min) show rapid swelling as evident in the FIGS. 7A to 7C, monitored over a 5 min time period. Expression of AQP-4 levels in stably transfected cells were confirmed using PCR (FIG. 8).

Compounds that affect cell swelling were evaluated for their ability to block cell swelling in AQP-4 +/+ vs AQP -/- stably transfected CHO cells.

Figure 9:
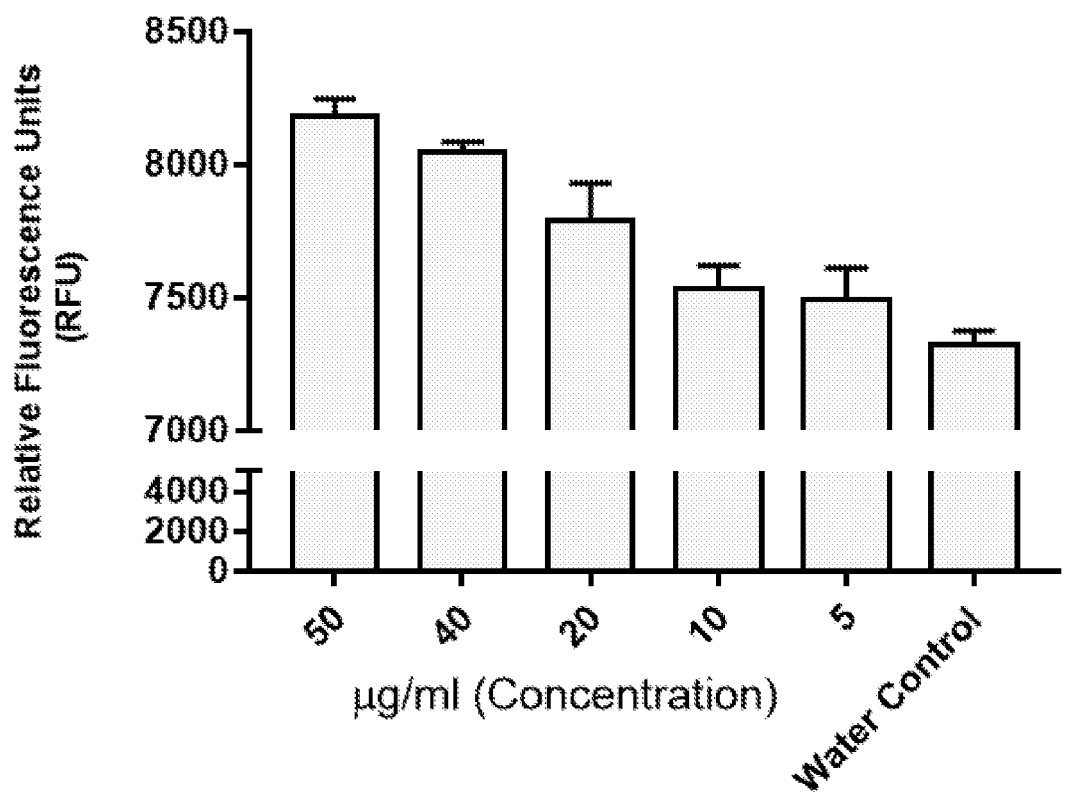
FIG. 9 is a graph that shows compound DHA-23 affect cell swelling as evaluated for their ability to block cell swelling in AQP-4 +/+ vs AQP −/− stably transfected CHO cells. The test compound DHA-23 revealed dose-related inhibition and the observed $IC_{50}$ was 0.7 μM.

Cell swelling was monitored by end-point assay using the fluorescent dye calcein. CHO cells transfected with hAQP-4 were exposed to water. When challenged with water, intact cells take up the dye whereas burst cells do not. Control cells overexpressing AQP-4 due to increased water flow swell rapidly following exposure to water and burst resulting in lower RFU signal. Inhibition of AQP-4 is expected to provide higher signal in end point assay. DEHA test compound DHA-23 (FIG. 9) reveal dose-related inhibition and the observed $IC_{50}$ was 0.7 µM.

Figure 10:
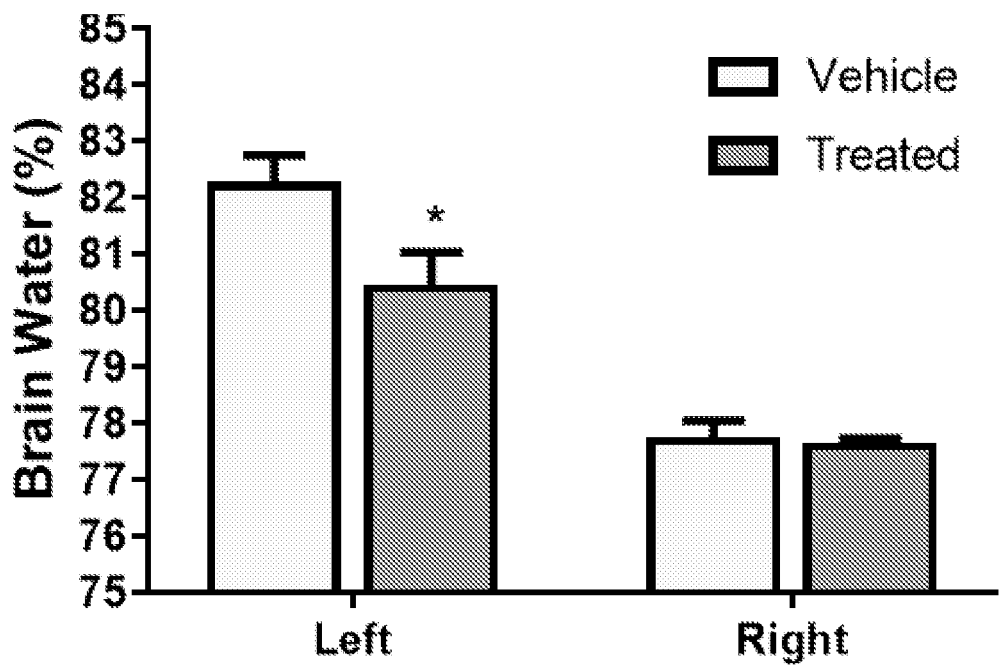
FIG. 10 is a graph that shows the effect of the test compound DHA-23 in vivo in a stroke animal model (MCAO occlusion).

In vivo pharmacological proof of activity in stroke animal model (MCAO occlusion): Male CD1 (25 to 30 g; n=10; CRL) mice were anesthetized and body temperature was maintained with a heating pad. The right common, external and internal carotid arteries (CCA, ECA, ICA) were exposed by a ventral midline incision. The CCA, distal ECA and pterygopalatine artery were tied off prior to bisection of the ECA. Middle cerebral artery occlusion (MCAO) was achieved by inserting the occluder retrograde into the external carotid artery (ECA) and advancing it into the ICA. The occluder was withdrawn following confirmation of drop in cerebral blood flow, the ECA was ligated and flow restored in the CCA/ICA. Following recovery, the test compounds were administered by tail vein (iv, 100 mg/kg) 2-4 hrs after surgery. Animals were euthanized after 24 hours and the brain was removed to get wet weight. The dry weight of the brain was obtained 24 hr later following overnight drying at 100.C. The absolute brain water content (WC) (%) was calculated using the following equation: WC (%)=[(WW−DW)/WW]×100. FIG. 10 is a graph that shows brain edema was determined by wet-dry method considered as gold standard for determining brain edema (fluid accumulation). Following reperfusion injury (left side) control animals reveal increased brain water accumulation compared to contralateral side (right side). Treatment with the test inhibitor significantly reduced brain edema (fluid accumulation) in the brain region (left) subjected to stroke by Middle Cerebral Artery Occlusion (n=5; p<0.05).

The overall objective of this project was identify a group of candidate selective AQP-4 inhibitors that reduce cellular swelling and to characterize their plasma elimination profile in order to select lead molecules. The selective AQP-4 inhibitors are optimized scaffolds identified and assessment for in vitro pharmacological properties and in vivo elimination kinetics.

Medicinal chemistry identify and select additional candidate AQP-4 inhibitors. The core scaffolds identified herein, and new scaffold derivatives can be designed using computational and medicinal chemistry programs that use structure-based screening. Hit compounds are then be synthesized in milligram quantities to investigate their AQP-4-related effects and pharmaceutical properties.

Perform structure-based screening of small-molecule library using the AQP-4 protein structure. The AQP-4 protein structure solved at 1.8 A resolution is available in the public domain.[50] Structure-based screenings using the Corestock subset of ChemBridge library (>640,000 compounds; contains over 810 novel scaffolds) has been performed and other datasets including DrugBank Asinex, NCI and ZINC will be searched for potential future screens. The virtual screen (VS) was performed in a sequential screening workflow using Schrodinger software that accounts for a balance of speed and accuracy.

Synthesize AQP-4 candidate inhibitors in sufficient quantity for in vitro and in vivo assessments. Compounds identified herein can be synthesized or purchased (2-5 mg) from commercial source (Chembridge library).

Modulators of AQP activity: Water channel modulators can be either inhibitors or inducers. To identify modulators of aquaporin activity, test compounds were screened for aquaporin selective splice variant.

Figure 11:
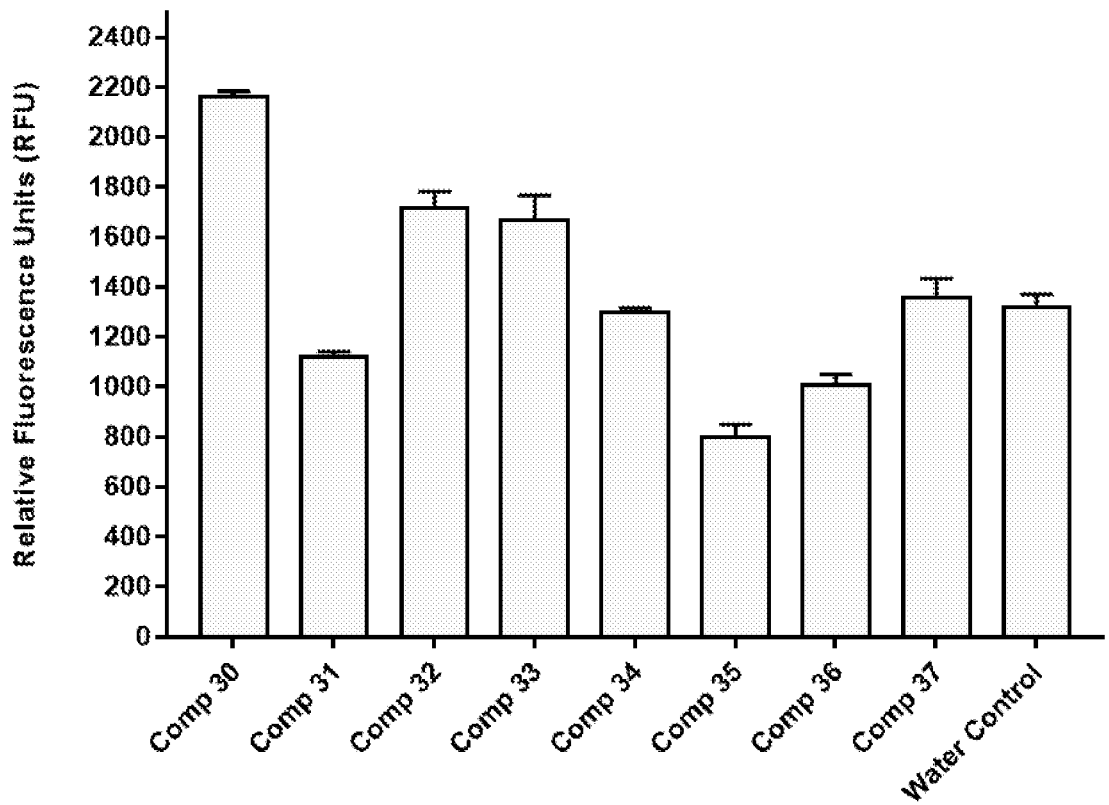
Figure 14A:
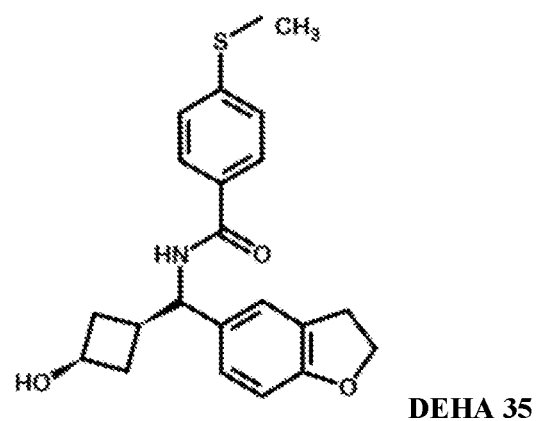

AQP-2 DHA-35. Using the kinetic screening assay described hereinabove, cells overexpressing AQP-2 were screened with test compounds of interest and their fluorescence signal were evaluated. DHA-35 was identified as an inhibitor. FIG. 14A shows the structure of DHA-35, and FIG. 11 is a graph that shows a kinetic screening assay described hereinabove, cells overexpressing AQP-2 were screened with test compounds of interest and their fluorescence signal were evaluated.

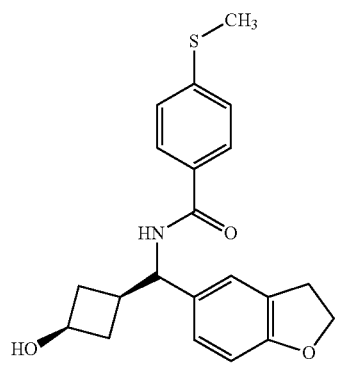 [SMILES: CSc1ccc(C(=O)NC(c2ccc3c(c2)CCO3)[C@H]2C[C@@H](O)C2)cc1]

Figure 12:
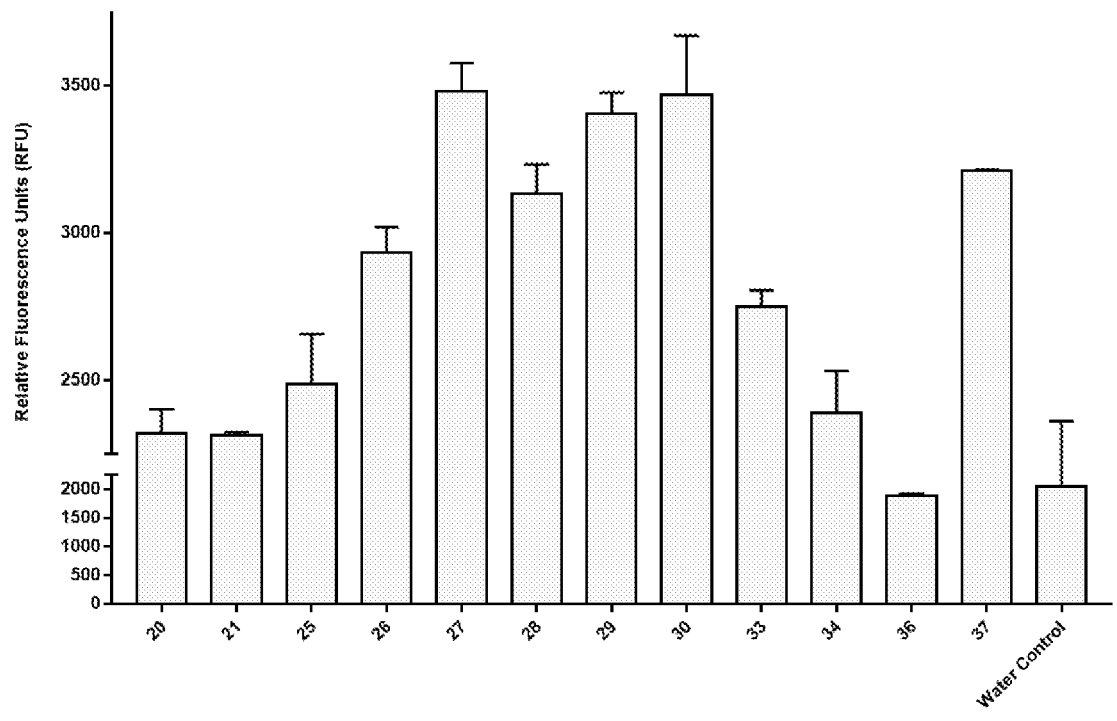
Figure 14B:
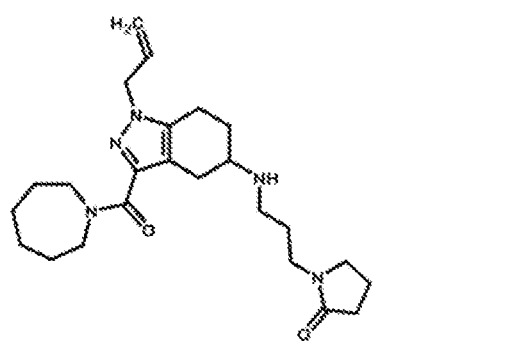

AQP-6 DHA-36. FIG. 12 shows the results of a kinetic screening assay described hereinabove, cells overexpressing AQP-6 were screened with test compounds of interest and their fluorescence signal were evaluated. FIG. 14B shows the structure for DHA-36 was identified as an inhibitor.

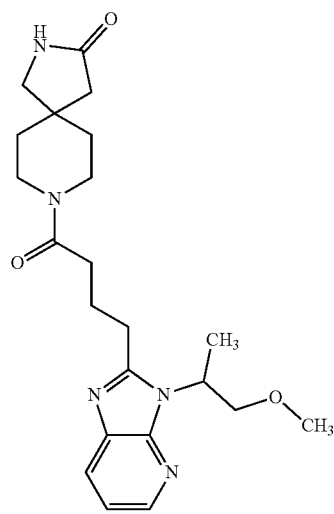 [SMILES: COCC(C)n1c(CCCC(=O)N2CCC3(CC2)CNC(=O)C3)nc2cccnc21]

Figure 13:
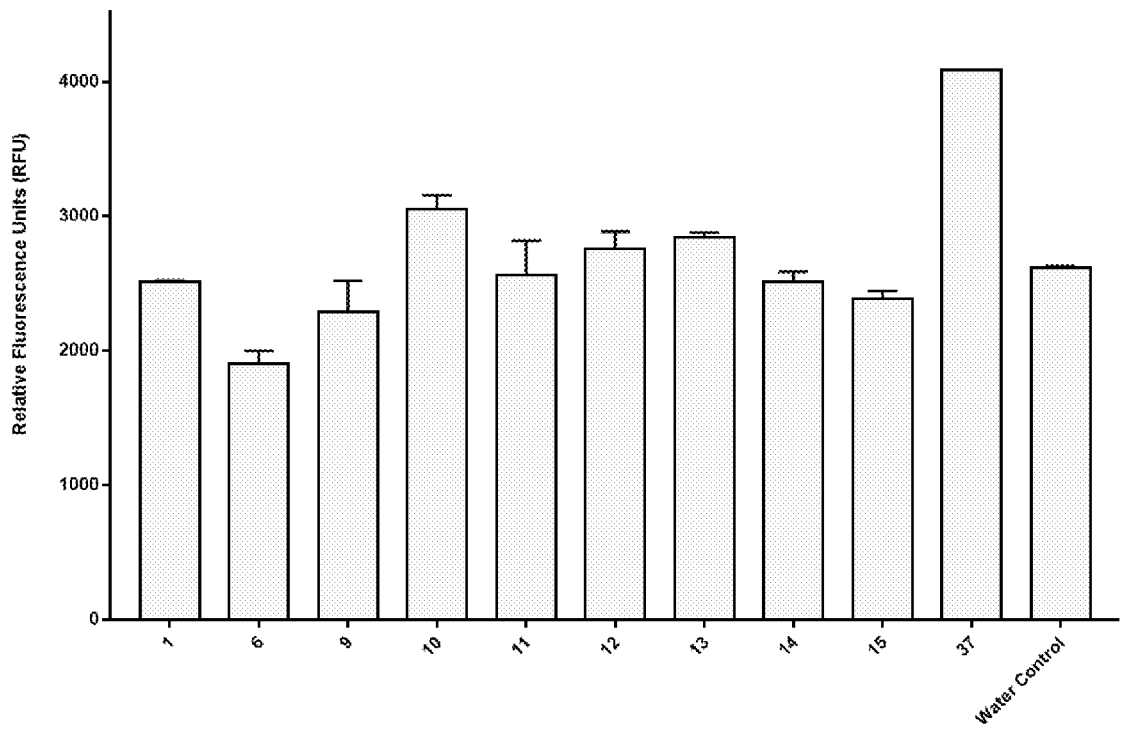
Figure 14C:
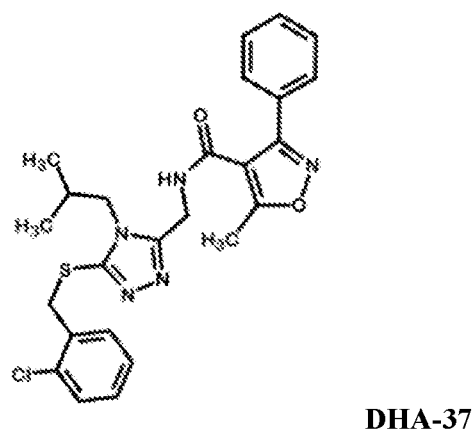
Figure 14D:
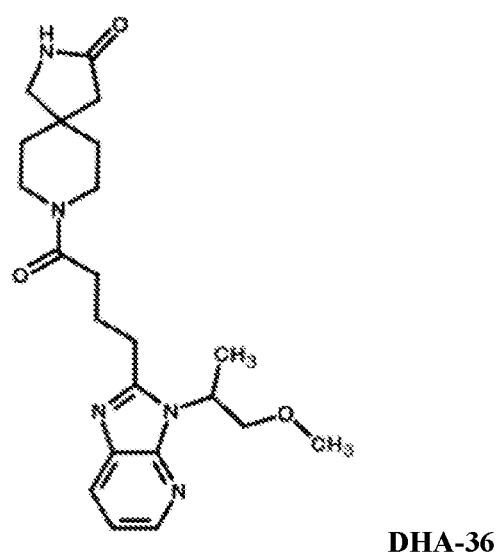

AQP-11 DHA-6 and DHA-37. FIG. 13 is a graph that shows the results of using the kinetic screening assay described hereinabove, cells overexpressing AQP-11 were screened with test compounds of interest and their fluorescence signal were evaluated. FIGS. 14C and 14C, respectively, shows the structures of DHA-6 and DHA-37 that were identified as modulators.

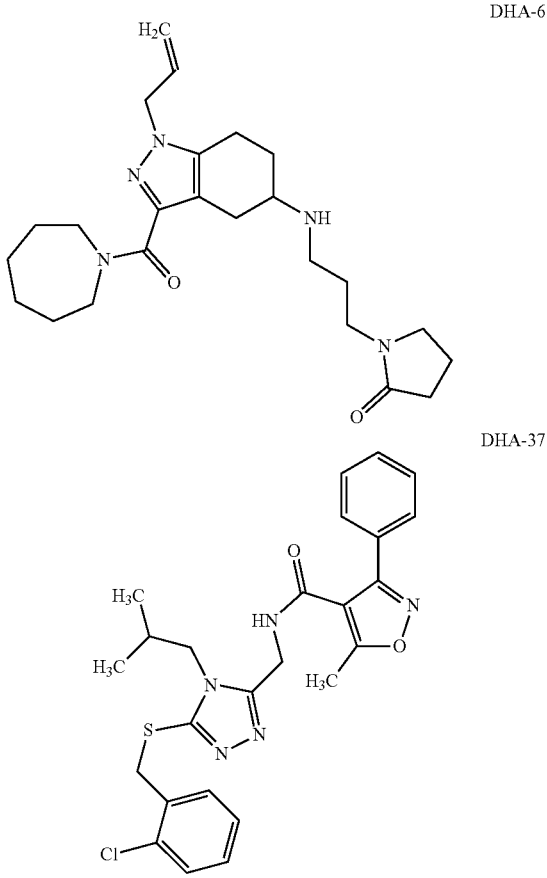

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1 Ed. Centers for Disease Control and Prevention (2017).
2 Hacke, W. et al. 'Malignant' middle cerebral artery territory infarction: clinical course and prognostic signs. Archives of neurology 53, 309-315 (1996).

3 Dostovic, Z., Dostovic, E., Smajlovic, D., Ibrahimagic, O. C. & Avdic, L. Brain Edema After Ischaemic Stroke. Med Arch 70, 339-341, doi:10.5455/medarh.2016.70.339-341 (2016).

4 Frank, J. I. Large hemispheric infarction, deterioration, and intracranial pressure. Neurology 45, 1286-1290 (1995).

5 Schwab, S., Aschoff, A., Spranger, M., Albert, F. & Hacke, W. The value of intracranial pressure monitoring in acute hemispheric stroke. Neurology 47, 393-398 (1996).

6 Manno, E. M., Adams, R. E., Derdeyn, C. P., Powers, W. J. & Diringer, M. N. The effects of mannitol on cerebral edema after large hemispheric cerebral infarct. Neurology 52, 583-587 (1999).

7 Vella, J., Zammit, C., Di Giovanni, G., Muscat, R. & Valentino, M. The central role of aquaporins in the pathophysiology of ischemic stroke. Front Cell Neurosci 9, 108, doi:10.3389/fncel.2015.00108 (2015).

8 Papadopoulos, M. C. & Verkman, A. S. Aquaporin-4 and brain edema. Pediatr Nephrol 22, 778-784, doi:10.1007/s00467-006-0411-0 (2007).

9 Ishibashi, K., Hara, S. & Kondo, S. Aquaporin water channels in mammals. Clin Exp Nephrol 13, 107-117, doi:10.1007/s10157-008-0118-6 (2009).

10 Verkman, A. S., Anderson, M. O. & Papadopoulos, M. C. Aquaporins: important but elusive drug targets. Nature reviews. Drug discovery 13, 259-277, doi:10.1038/nrd4226 (2014).

11 Noel, G., Stevenson, S. & Moukhles, H. A high throughput screen identifies chemical modulators of the laminin-induced clustering of dystroglycan and aquaporin-4 in primary astrocytes. PLoS One 6, e17559, doi:10.1371/journal.pone.0017559 (2011).

12 Mozaffarian, D. et al. Heart disease and stroke statistics-2015 update: a report from the american heart association. Circulation 131, e29-e322, doi:10.1161/cir.0000000000000152 (2015).

13 Ovbiagele, B. et al. Forecasting the future of stroke in the United States: a policy statement from the American Heart Association and American Stroke Association. Stroke 44, 2361-2375, doi:10.1161/STR.0b013e31829734f2 (2013).

14 Powers, W. J. et al. 2015 American Heart Association/American Stroke Association Focused Update of the 2013 Guidelines for the Early Management of Patients With Acute Ischemic Stroke Regarding Endovascular Treatment: A Guideline for Healthcare Professionals From the American Heart Association/American Stroke Association. Stroke 46, 3020-3035, doi:10.1161/str.0000000000000074 (2015).

15 Siegel, J. et al. Update on Neurocritical Care of Stroke. Current cardiology reports 19, 67, doi:10.1007/s11886-017-0881-7 (2017).

16 Stankowski, J. N. & Gupta, R. Therapeutic targets for neuroprotection in acute ischemic stroke: lost in translation? Antioxidants & redox signaling 14, 1841-1851, doi:10.1089/ars.2010.3292 (2011).

17 Grupke, S., Hall, J., Dobbs, M., Bix, G. J. & Fraser, J. F. Understanding history, and not repeating it. Neuroprotection for acute ischemic stroke: From review to preview. Clinical neurology and neurosurgery 129c, 1-9, doi:10.1016/j.clineuro.2014.11.013 (2015).

18 Lai, T. W., Zhang, S. & Wang, Y. T. Excitotoxicity and stroke: identifying novel targets for neuroprotection. Progress in neurobiology 115, 157-188 (2014).

19 Remedy Pharmaceuticals. White paper: a guide to understanding large hemispheric infarction. (2016).

20 Vahedi, K. et al. Early decompressive surgery in malignant infarction of the middle cerebral artery: a pooled analysis of three randomised controlled trials. The Lancet. Neurology 6, 215-222, doi:10.1016/s1474-4422(07)70036-4 (2007).

21 Kasner, S. E. et al. Predictors of fatal brain edema in massive hemispheric ischemic stroke. Stroke 32, 2117-2123 (2001).

22 Wijdicks, E. F. Management of massive hemispheric cerebral infarct: is there a ray of hope? Mayo Clinic proceedings 75, 945-952 (2000).

23 Dirnagl, U., Iadecola, C. & Moskowitz, M. A. Pathobiology of ischaemic stroke: an integrated view. Trends in neurosciences 22, 391-397 (1999).

24 White, B. C. et al. Brain ischemia and reperfusion: molecular mechanisms of neuronal injury. Journal of the neurological sciences 179, 1-33 (2000).

25 Mehta, S. L., Manhas, N. & Raghubir, R. Molecular targets in cerebral ischemia for developing novel therapeutics. Brain research reviews 54, 34-66, doi:10.1016/j.brainresrev.2006.11.003 (2007).

26 Stokum, J. A., Kurland, D. B., Gerzanich, V. & Simard, J. M. Mechanisms of astrocyte-mediated cerebral edema. Neurochemical research 40, 317-328, doi:10.1007/s11064-014-1374-3 (2015).

27 Previch, L. E. et al. Progress in AQP Research and New Developments in Therapeutic Approaches to Ischemic and Hemorrhagic Stroke. International journal of molecular sciences 17, doi:10.3390/ijms17071146 (2016).

28 Rash, J. E., Yasumura, T., Hudson, C. S., Agre, P. & Nielsen, S. Direct immunogold labeling of aquaporin-4 in square arrays of astrocyte and ependymocyte plasma membranes in rat brain and spinal cord. Proceedings of the National Academy of Sciences of the United States of America 95, 11981-11986 (1998).

29 Ames, A., 3rd, Wright, R. L., Kowada, M., Thurston, J. M. & Majno, G. Cerebral ischemia. II. The no-reflow phenomenon. The American journal of pathology 52, 437-453 (1968).

30 Choi, D. W. & Rothman, S. M. The role of glutamate neurotoxicity in hypoxic-ischemic neuronal death. Annual review of neuroscience 13, 171-182, doi:10.1146/annurev.ne.13.030190.001131 (1990).

31 Yao, X., Derugin, N., Manley, G. T. & Verkman, A. S. Reduced brain edema and infarct volume in aquaporin-4 deficient mice after transient focal cerebral ischemia. Neuroscience letters 584, 368-372, doi:10.1016/j.neulet.2014.10.040 (2015).

32 Manley, G. T. et al. Aquaporin-4 deletion in mice reduces brain edema after acute water intoxication and ischemic stroke. Nat Med 6, 159-163, doi:10.1038/72256 (2000).

33 Akdemir, G., Ratelade, J., Asavapanumas, N. & Verkman, A. S. Neuroprotective effect of aquaporin-4 deficiency in a mouse model of severe global cerebral ischemia produced by transient 4-vessel occlusion. Neuroscience letters 574, 70-75, doi:10.1016/j.neulet.2014.03.073 (2014).

34 Haj-Yasein, N. N. et al. Glial-conditional deletion of aquaporin-4 (Aqp4) reduces blood-brain water uptake and confers barrier function on perivascular astrocyte endfeet. Proceedings of the National Academy of Sciences of the United States of America 108, 17815-17820, doi:10.1073/pnas.1110655108 (2011).

35 Hirt, L. et al. Improved long-term outcome after transient cerebral ischemia in aquaporin-4 knockout mice. Journal of cerebral blood flow and metabolism: official journal of the International Society of Cerebral Blood Flow and Metabolism 37, 277-290, doi:10.1177/0271678x15623290 (2017).

36 Katada, R. et al. Greatly improved survival and neuroprotection in aquaporin-4-knockout mice following global cerebral ischemia. FASEB journal: official publication of the Federation of American Societies for Experimental Biology 28, 705-714, doi:10.1096/fj.13-231274 (2014).

37 Wang, Z. et al. Potential contribution of hypoxia-inducible factor-1alpha, aquaporin-4, and matrix metalloproteinase-9 to blood-brain barrier disruption and brain edema after experimental subarachnoid hemorrhage. Journal of molecular neuroscience: MN 48, 273-280, doi:10.1007/s12031-012-9769-6 (2012).

38 Yang, C. et al. Aquaporin-4 knockdown ameliorates hypoxic-ischemic cerebral edema in newborn piglets. IUBMB life 67, 182-190, doi:10.1002/iub.1356 (2015).

39 Stokum, J. A. et al. Heterogeneity of aquaporin-4 localization and expression after focal cerebral ischemia underlies differences in white versus grey matter swelling. Acta neuropathologica communications 3, 61, doi:10.1186/s40478-015-0239-6 (2015).

40 Igarashi, H., Huber, V. J., Tsujita, M. & Nakada, T. Pretreatment with a novel aquaporin 4 inhibitor, TGN-020, significantly reduces ischemic cerebral edema. Neurological sciences: official journal of the Italian Neurological Society and of the Italian Society of Clinical Neurophysiology 32, 113-116, doi:10.1007/s10072-010-0431-1 (2011).

41 Jin, B. J., Zhang, H., Binder, D. K. & Verkman, A. S. Aquaporin-4-dependent K(+) and water transport modeled in brain extracellular space following neuroexcitation. The Journal of general physiology 141, 119-132, doi:10.1085/jgp.201210883 (2013).

42 Yu, H. et al. Aquaporin 4 inhibition decreased synthesis of cytokines by acetazolamide in the hippocampus of rats with pentrazol-induced chronic epilepsy. Genetics and molecular research: GMR 15, doi:10.4238/gmr.15039012 (2016).

43 Sturdivant, N. M., Smith, S. G., Ali, S. F., Wolchok, J. C. & Balachandran, K. Acetazolamide Mitigates Astrocyte Cellular Edema Following Mild Traumatic Brain Injury. Scientific reports 6, 33330, doi:10.1038/srep33330 (2016).

44 Kamegawa, A., Hiroaki, Y., Tani, K. & Fujiyoshi, Y. Two-dimensional crystal structure of aquaporin-4 bound to the inhibitor acetazolamide. Microscopy (Oxford, England) 65, 177-184, doi:10.1093/jmicro/dfv368 (2016).

45 Uldall, M., Botfield, H., Jansen-Olesen, I., Sinclair, A. & Jensen, R. Acetazolamide lowers intracranial pressure and modulates the cerebrospinal fluid secretion pathway in healthy rats. Neuroscience letters 645, 33-39, doi:10.1016/j.neulet.2017.02.032 (2017).

46 Mehta, R. I. et al. Sur1-Trpm4 Cation Channel Expression in Human Cerebral Infarcts. J Neuropathol Exp Neurol 74, 835-849, doi:10.1097/NEN.0000000000000223 (2015).

47 Alberga, D. et al. A new gating site in human aquaporin-4: Insights from molecular dynamics simulations. Biochim Biophys Acta 1838, 3052-3060, doi:10.1016/j.bbamem.2014.08.015 (2014).

48 Yukutake, Y., Hirano, Y., Suematsu, M. & Yasui, M. Rapid and reversible inhibition of aquaporin-4 by zinc. Biochemistry 48, 12059-12061, doi:10.1021/bi901762y (2009).

49 Yukutake, Y. & Yasui, M. Regulation of water permeability through aquaporin-4. Neuroscience 168, 885-891, doi:10.1016/j.neuroscience.2009.10.029 (2010).

50 Ho, J. D. et al. Crystal structure of human aquaporin 4 at 1.8 A and its mechanism of conductance. Proceedings of the National Academy of Sciences of the United States of America 106, 7437-7442, doi:10.1073/pnas.0902725106 (2009).

51 Halgren, T. A. Identifying and characterizing binding sites and assessing druggability. J Chem Inf Model 49, 377-389, doi:10.1021/ci800324m (2009).

52 Halgren, T. New method for fast and accurate binding-site identification and analysis. Chem Biol Drug Des 69, 146-148, doi:10.1111/j.1747-0285.2007.00483.x (2007).

53 Alvarez-Leefmans, F., Altamirano, J. & Crowe, W. Use of ion-selective microelectrodes and fluorescent probes to measure cell volume. Methods in Neurosciences 27, 361-391 (1995).

54 Rao, K. V., Reddy, P. V., Curtis, K. M. & Norenberg, M. D. Aquaporin-4 expression in cultured astrocytes after fluid percussion injury. J Neurotrauma 28, 371-381, doi:10.1089/neu.2010.1705 (2011).

55 Parry, T. J. et al. Effects of neuregulin GGF2 (cimaglermin alfa) dose and treatment frequency on left ventricular function in rats following myocardial infarction. Eur J Pharmacol 796, 76-89, doi:10.1016/j.ejphar.2016.12.024 (2017).

What is claimed is:

1. A method of treating a subject in need of treatment for a disease or condition in which an Aquaporin-2, an Aquaporin-4, an Aquaporin-6, or an Aquaporin-11 is in need of modulation comprising:

providing the subject with a therapeutically effective amount of an Aquaporin-2, an Aquaporin-4, an Aquaporin-6, or an Aquaporin-11, inhibitor or modulator selected from at least one of:

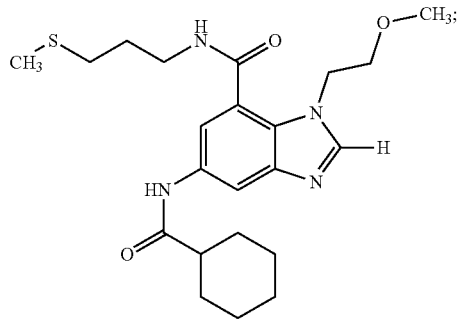

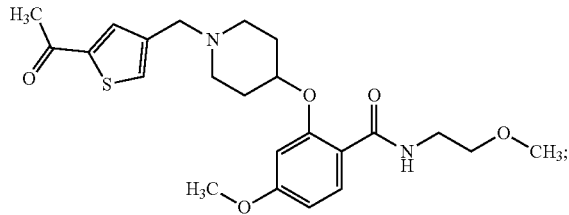

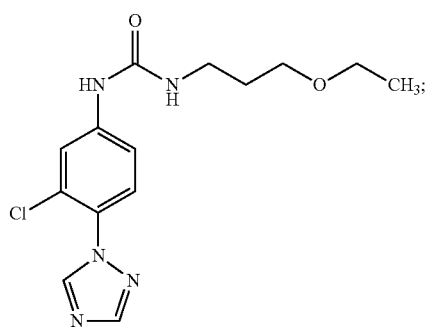
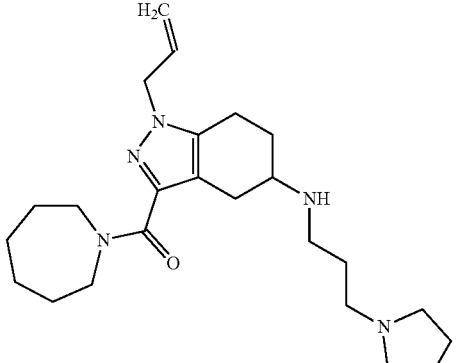

2. The method of claim 1, wherein the Aquaporin-2, Aquaporin-4, Aquaporin-6, or Aquaporin-11 inhibitor is adapted for oral, enteral, parenteral, intravenous, subcutaneous, intramuscular, pulmonary, or rectal administration.

3. The method of claim 1, wherein the Aquaporin-2, Aquaporin-4, Aquaporin-6, or Aquaporin-11 inhibitor is provided in an amount of 1 microgram to 1 gram per dose.

4. The method of claim 1, wherein the patient has been treated previously with at least one of an osmotic agent, barbiturates, steroids, or diuretics and the subject has become refractory to that treatment.

5. The method of claim 1, wherein the Aquaporin-2, Aquaporin-4, Aquaporin-6, or Aquaporin-11 inhibitor has a potency in the range of 1-10 μM, 0.1-100 μM or 5-9 μM.

6. The method of claim 1, wherein the Aquaporin-2, Aquaporin-4, Aquaporin-6, or Aquaporin-11 inhibitor inhibits perivascular astrocyte swelling.

7. The method of claim 1, wherein the Aquaporin-2, Aquaporin-4, Aquaporin-6, or Aquaporin-11 inhibitor reduces brain edema and infarct size after stroke.

8. The method of claim 1, wherein the Aquaporin-2, Aquaporin-4, Aquaporin-6, or Aquaporin-11 is an Aquaporin splice variant.

* * * * *